US00PP18914P2

(12) United States Plant Patent
Kraan

(10) Patent No.: US PP18,914 P2
(45) Date of Patent: Jun. 10, 2008

(54) ROSE PLANT NAMED 'BOKRARUNNER'

(50) Latin Name: *Rosa hybrida*
Varietal Denomination: Bokrarunner

(75) Inventor: Kees Jan Kraan, Ter Aar (NL)

(73) Assignee: Boot & Co. Nurseries BV, Boskoop (NL)

( * ) Notice: Subject to any disclaimer, the term of this patent is extended or adjusted under 35 U.S.C. 154(b) by 0 days.

(21) Appl. No.: 11/602,933

(22) Filed: Nov. 21, 2006

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para

(57) ABSTRACT

A new cultivar of *Rosa* plant named 'Bokrarunner' that is characterized by dark green glossy leaves, dark pink-red flowers in large panicles and long flower life.

1 Drawing Sheet

Botanical classification: *Rosa hybrida.*
Variety denomination: 'Bokrarunner'.

BACKGROUND OF THE INVENTION

The present invention relates to a new and distinct cultivar of Rose plant botanically known as *Rosa* and hereinafter referred to by the cultivar name 'Bokrarunner'.

The new cultivar is the product of a breeding program conducted by the inventor in a cultivated area of Boskoop, The Netherlands. The objective of the breeding program was to develop new rose cultivars with a compact habit and long flower life. 'Bokrarunner' is a hybrid that originated from the hybridization of the female or seed parent *Rosa* 'Ivtagolf' (U.S. Plant Pat. No. 11,371) and the male or pollen parent, an unnamed proprietary seedling. The cultivar 'Bokrarunner' was selected by the inventor in the Summer of 1996 as a single plant within the progeny of the stated cross in a controlled environment of Boskoop, The Netherlands.

The closest comparison plant is *Rosa* 'Bokrarug' (U.S. Plant Pat. No. 14,016) 'Bokrarunner' is distinguishable from 'Bokrarug' in having smaller pink-red flowers. The flowers of 'Bokrarug' are white.

The new cultivar 'Bokrarunner' is distinguishable from the male parent in having pink-red flowers. The flowers of the male parent are red.

The new cultivar 'Bokrarunner' is distinguishable from the female parent 'Ivtagolf' in having smaller pink-red flowers. The flowers of 'Ivtagolf' are white.

Asexual reproduction by cuttings of the new cultivar 'Bokrarunner' was first performed in 2003 in Boskoop, The Netherlands by the inventor. Since that time, under careful observation, the unique characteristics of the new Rose cultivar have been uniform, stable and reproduced true to type in successive generations of asexual reproduction.

SUMMARY OF THE INVENTION

The following represent the distinguishing characteristics of the new *Rosa* cultivar 'Bokrarunner'. These traits in combination distinguish 'Bokrarunner' as a new and distinct cultivar apart from all other existing varieties of *Rosa* known to the inventor. 'Bokrarunner' has not been tested under all possible conditions and phenotypic differences may be observed with variations in environmental, climatic, and cultural conditions, however, without any variance in genotype.

1. *Rosa* 'Bokrarunner' exhibits dark green glossy leaves.
2. *Rosa* 'Bokrarunner' exhibits dark pink-red flowers in large panicles.
3. *Rosa* 'Bokrarunner' exhibits long flower life.

BRIEF DESCRIPTION OF THE DRAWING

The accompanying photograph illustrates the distinguishing traits of *Rosa* 'Bokrarunner'. The plants in the photograph show an overall view of one year old field grown plants. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rosa* cultivar named 'Bokrarunner'. Data was collected in Boskoop, The Netherlands from one-year-old field grown plants. The time of year was August and the temperatures ranged from 14-32° Centigrade during the day, and 7-14° Centigrade during the night. The light level was natural outdoor light and there were no photoperiodic treatments or growth retardants used. Color determinations are in accordance with The Royal Horticultural Society Colour Chart except where general color terms of ordinary dictionary significance are used. The growing requirements are similar to the species.

Botanical classification: *Rosa hybrida* 'Bokrarunner'.
Type: Perennial shrub.
Use: Ornamental.
Parentage: 'Bokrarunner' is a hybrid plant that resulted from the hybridization of the following parent plants:
*Female parent.*—*Rosa* 'Ivtagolf'.
*Male parent.*—An unnamed proprietary rose seedling.

Vigor: Moderate.
Growth rate: Approximately 12 cm. per month in spring.
Plant shape: Broad-obovate.
Suitable container size: Field grown.
Height: 35 cm. in height.
Width: 36 cm. in width.
Hardiness: USDA Zone 5.
Propagation: Softwood cuttings.
Time to initiate roots: Approximately 60 days are required to produce roots on an initial cutting.
Crop time: Approximately 12 months are required to achieve a finished plant from a rooted cutting.
Root system: Fine and fibrous.
Stem:
*Branching habit.*—Moderately free branching.
*Average number of lateral branches.*—Five.
*Pinching.*—No.
*Stem diameter.*—Approximately 5 mm. in diameter.
*Stem length.*—Approximately 24.8 cm. in length.
*Stem strength.*—Strong.
*Stem color.*—144B.
*Pubescence.*—Absent.
*Internode length.*—Approximately 3.5 cm. between nodes.
*Shape.*—Rounded, glossy, and sparsely covered with spines.
*Surface.*—Glabrous and dull and covered with sharp spines.
*Number of spines.*—1 per cm. of stem length.
*Spine dimensions.*—Approximately 5 mm. in length and 6 mm. in width.
*Color of spines.*—178A.
Foliage:
*Durability to foliage stresses.*—Moderate to high.
*Texture.*—Smooth and glossy.
*Leaf arrangement.*—Alternate.
*Compound or single.*—Compound.
*Quantity of leaves per lateral branch.*—Approximately 8.
*Quantity of leaflets per leaf.*—Average 6.
*Leaf margin.*—Serrate.
*Leaf shape.*—Ovate.
*Leaf tip.*—Acute.
*Leaf base.*—Rounded.
*Leaf length.*—Leaf, 8.6 cm; leaflet, 2.9 cm.
*Leaf width.*—Leaf, 5.4 cm; leaflet, 2.0 cm.
*Pubescence.*—Absent.
*Vein pattern.*—Pinnate.
*Leaf color young, upper surface.*—143A.
*Leaf color young, lower surface.*—146B.
*Leaf color mature, upper surface.*—141A.
*Leaf color mature, lower surface.*—144A.
*Vein color, upper side.*—144B.
*Vein color, under side.*—144C.
*Leaf attachment.*—Petiolate.
*Petiole dimensions.*—1.7 cm. in length and 1.0 mm. in width.
*Petiole color.*—144B.
*Stipules.*—1.8 cm. in length, 4 mm. in width, upper side 144B, lower side 144B.
*Other.*—Leaf midrib sparsely covered with small spines, 1.0 mm. in length, color 175B.
Flower:
*Flower arrangement.*—Terminal compound corymb.
*Inflorescence type.*—Clustered.
*Inflorescence height.*—Approximately 10.2 cm. in height.
*Inflorescence diameter.*—Approximately 15.8 cm. in diameter.
*Quantity of flowers per inflorescence.*—Approximately 22.
*Flower type.*—Single and rotate.
*Flowering habit.*—Once a year.
*Quantity of flowers per lateral stem.*—Approximately 22.
*Quantity of flower buds per lateral stem.*—Approximately 12.
*Quantity of flowers and buds per plant.*—Approximately 170.
*Flowering season.*—Mid June to October.
*Time to flower (response time).*—Approximately 8 months.
*Rate of flower opening.*—Approximately 60% of the flowers are opened at once.
*Fragrance.*—Absent.
*Flower bud length.*—1.6 cm. in length.
*Flower bud diameter.*—8 mm. in diameter.
*Flower bud shape.*—Ovate.
*Bud color.*—144A with tinges of 176B.
*Flower aspect.*—Upward to outward.
*Flower shape.*—Cup-shaped, rotate.
*Flower dimensions.*—4.9 cm. in diameter and 2.8 cm. in height.
*Flower longevity.*—Lasts a few days on plant.
*Petal color when opening (under side).*—53C.
*Petal color when opening (upper side).*—N57A.
*Petal color fully opened (upper side).*—N57A.
*Petal color fully opened (under side).*—N57B.
*Petal color, fading to.*—N57C.
*Petal appearance.*—Rotate.
*Persistent or self-cleaning.*—Self-cleaning.
*Petal texture.*—Glabrous.
*Petal arrangement.*—Rotate.
*Number of petals.*—Seven in number.
*Petals fused or unfused.*—Unfused.
*Petal shape.*—Obcordate.
*Petal margin.*—Entire.
*Petal apex.*—Shallowly retuse.
*Petal dimensions.*—2.6 cm. in length and 2.0 cm. in width.
*Petaloids.*—Absent.
*Pedicel dimensions.*—2.1 cm. in length and 1.5 mm. in diameter.
*Pedicel angle.*—30°.
*Pedicel color.*—144A to 178A to 178B.
*Pedicel strength.*—Strong.
*Sepal color, young (upper side).*—143C.
*Sepal color, young (under side).*—144A.
*Sepal color, mature (upper side).*—143C.
*Sepal color, mature (under side).*—144A.
*Sepal surface.*—Dull and pubescent.
*Sepal arrangement.*—Rotate and reflexed.
*Number of sepals.*—Five.
*Sepal shape.*—Ovate.
*Sepal margin.*—Entire.
*Sepal apex.*—Narrow acminate.
*Sepal base.*—Broad cuneate.
*Sepal dimensions.*—1.4 cm. in length and 5 mm. in width.
*Petaloids.*—Absent.
*Calyx shape.*—Rotate; reflexed.

*Calyx dimensions.*—1.2 cm. in length and 1.1 cm. in diameter.
*Peduncle dimensions.*—4.7 cm in length; 2.5 mm in width.
*Peduncle angle.*—Central 0°, secondary 30°.
*Peduncle strength.*—Strong.
*Peduncle color.*—144B.

Reproduction organs:
*Stamen number.*—Approximately 80.
*Anther shape.*—Basifixed, kidney shape.
*Anther dimensions.*—5 mm. in diameter and 1 mm. in length.
*Anther color.*—22A.
*Amount of pollen.*—Low.
*Pollen color.*—13A.
*Pistil number.*—15 in number.
*Pistil length.*—3 mm.
*Stigma shape.*—Irregular and flattened.
*Stigma color.*—153A.
*Style length.*—2.5 mm.
*Style color.*—144C.
*Ovary color.*—143A.

Seed: Seed production has not been observed.

What is claimed is:

1. A new and distinct variety of *Rosa* plant named 'Bokrarunner' as described and illustrated.

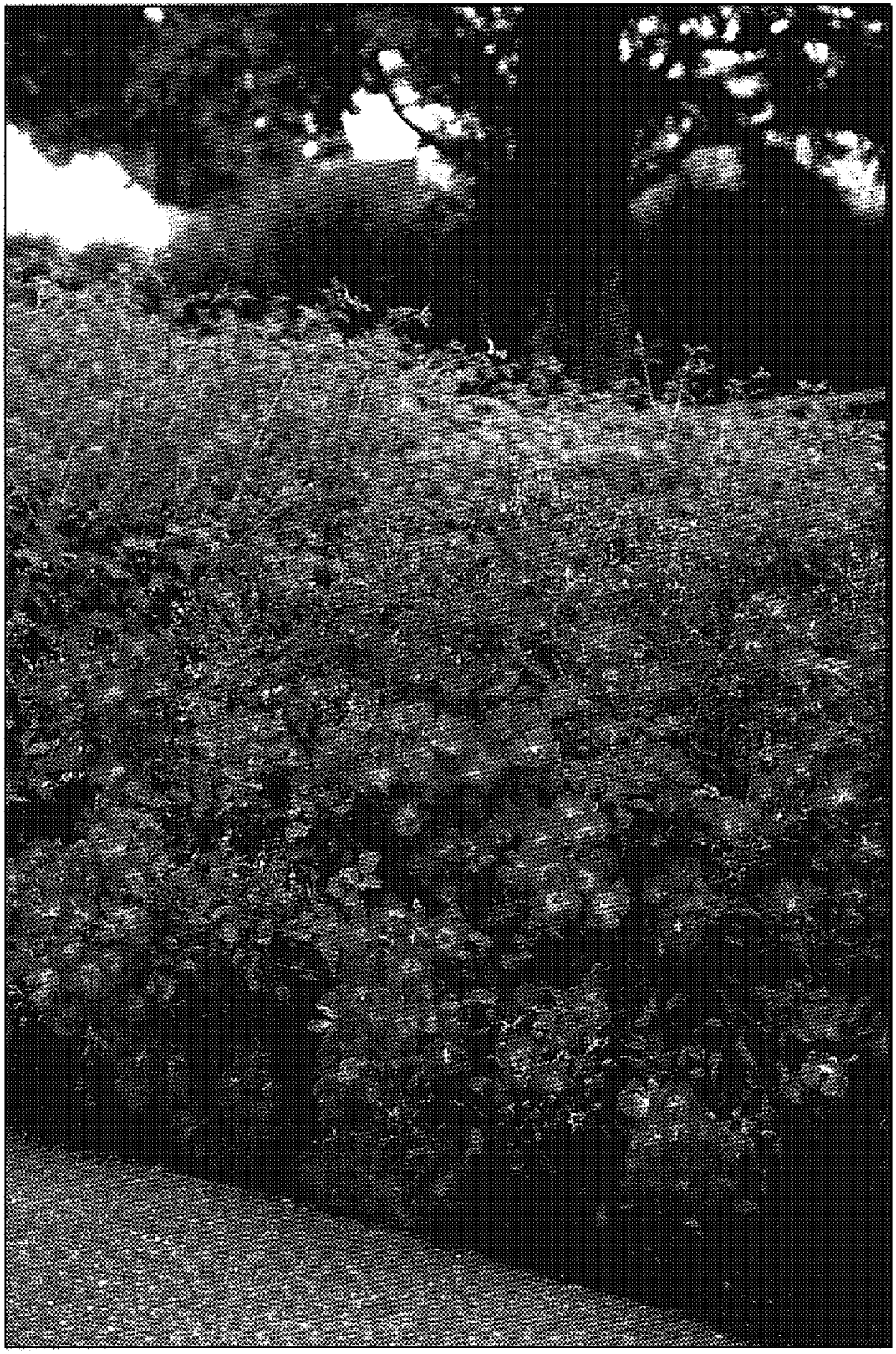

* * * * *